United States Patent [19]
Orr et al.

[11] Patent Number: 5,480,632
[45] Date of Patent: Jan. 2, 1996

[54] NON-AQUEOUS COSMETIC COMPOSITIONS WITH HIGH SOLIDS CONTENT

[75] Inventors: Carl C. Orr, Raleigh, N.C.; John Caradonna, Memphis, Tenn.; Robert J. Edmundson, Germantown, Tenn.; Terry C. Jacks, Memphis, Tenn.

[73] Assignee: Maybelline, Inc., Wilmington, Del.

[21] Appl. No.: 87,357

[22] Filed: Jul. 8, 1993

Related U.S. Application Data

[63] Continuation of Ser. No. 97,036, Sep. 16, 1987, abandoned.

[51] Int. Cl.$^6$ .......................... A61K 7/032; A61K 31/74
[52] U.S. Cl. .................. 424/63; 424/70.7; 424/78.03
[58] Field of Search .............................. 424/63, 69, 64, 424/78.03, 70.7

[56] References Cited

U.S. PATENT DOCUMENTS

| Re. 29,871 | 12/1978 | Papantoniou | 424/DIG. 5 |
|---|---|---|---|
| 4,105,578 | 8/1978 | Finlayson et al. | 252/316 |
| 4,305,961 | 12/1981 | Tsutsumi | 424/63 |
| 4,349,389 | 9/1982 | Schofield | 523/200 |
| 4,695,452 | 9/1987 | Gannis | 424/DIG. 5 |
| 4,800,076 | 1/1989 | Bhat | 424/69 |
| 4,877,604 | 10/1985 | Schlossman | 424/64 |

*Primary Examiner*—Thurman K. Page
*Assistant Examiner*—Sally Gardner
*Attorney, Agent, or Firm*—Sherman and Shalloway

[57] ABSTRACT

A non-aqueous cosmetic composition suitable as mascara, eyeliner, or lipstick comprising a dispersing agent in an amount sufficient to permit a high content of cosmetically acceptable solids, e.g. colorants, waxes, dry powders and solids.

3 Claims, No Drawings

NON-AQUEOUS COSMETIC COMPOSITIONS WITH HIGH SOLIDS CONTENT

This application is a continuation of application Ser. No. 07/097,036, filed Sep. 16, 1987, now abandonded.

BACKGROUND OF THE INVENTION

This invention relates to non-aqueous cosmetic compositions such as mascara, eyeliner, and lipstick containing amounts of a dispersing agent sufficient to allow higher amounts of cosmetically acceptable solids, colorants, waxes, dry powders and the like compared to a conventional non-aqueous cosmetic composition.

Non-aqueous cosmetic products such as mascara, eyeliner, and lipstick contain colorants i.e., organic and inorganic pigments in a non-aqueous cosmetic carrier containing cosmetically acceptable solvents. Solsperse hyperdispersants are a group of dispersing aids available from ICI Americas Inc. for use with non-aqueous solvents in air-drying paint systems, such as air-drying alkyd paints, chlorinated rubber paints and solvent-based vinyl paints. There is no disclosure of the use of Solsperse hyperdispersants in cosmetics.

SUMMARY OF THE INVENTION

The present invention provides a non-aqueous cosmetic composition having a high solid content comprising cosmetically acceptable liquids, solvents, colorants, waxes, dry powders and solids in a non-aqueous cosmetic carrier in admixture with a sufficient amount of a dispersing agent to permit an increase in the amount of cosmetically acceptable colorants, waxes, dry powders and solids from the amounts originally present in the corresponding cosmetic composition by from about 10 percent by weight to about 55 percent by weight.

The non-aqueous compositions of this invention may be formulated as mascaras, eyeliners or lipsticks.

DETAILED DESCRIPTION OF THE INVENTION

The term "non-aqueous" as used herein in reference to the cosmetic compositions and cosmetic carriers used in the cosmetic compositions of this invention means a substantially water-free composition, i.e. less than about 1% by weight of water. While no water is added to the cosmetic compositions or carrier, no attempt is made to rigorously exclude water which may be associated with the ingredients used in the compositions of the present invention.

The term "cosmetic carrier" as used herein means a cosmetic formula which has conventionally been used in the art to serve as a vehicle for colorants i.e. organic and inorganic pigments and to cover up imperfections on the skin. The conventional carriers may contain cosmetically acceptable solvents, liquids or oils, waxes, dry powders and solids. The dry powders and solids may be suspended in lipophilic emulsions or dispersions formed from mixtures of oils and waxes. See for example the four volume set entitled "Cosmetics, Science and Technology", Volumes I and II, M. S. Batsam and E. Sagarin, eds., Wiley-Interscience, 1972, and THE CHEMISTRY AND MANUFACTURE OF COSMETICS, Volumes III and IV, 2nd Ed., M. deNavarre, ed., Continental Press, 1975 for disclosures of conventional non-aqueous cosmetic compositions and cosmetic carriers.

The non-aqueous cosmetic compositions of the present invention incorporate amounts of a dispersing agent sufficient to enable an increase in the amounts of cosmetically acceptable solids, waxes, colorants, and dry powders from the amounts originally present in a non-aqueous cosmetic composition by from about 10 percent by weight to about 55 percent by weight, while maintaining the cosmetic characteristics of the cosmetic compositions. In the preferred eyeliner and mascara cosmetic compositions of the present invention, the increase in cosmetically acceptable solids, waxes, colorants and dry powders from the amounts originally present in a non-aqueous cosmetic composition is in the range of about 10 percent by weight to about 25 percent by weight. See, for example Comparative Examples 1 and 2 hereinafter. In the preferred lipstick cosmetic compositions of the present invention, the increase in the cosmetically acceptable solids, waxes, colorants and dry powders from the amounts originally present in the cosmetic compositions is in the range of about 10 percent by weight to about 55 weight percent. See Example 10 hereinafter.

The non-aqueous compositions of the present invention provide higher content of cosmetically acceptable solids, waxes, colorants, pigments and dry powders while also allowing use of smaller amounts of solvents, e.g. odorless petroleum distillate such as Shell Sol 71, for mascara, and eyeliner and liquids, e.g., castor oil, for lipsticks. The non-aqueous cosmetic compositions of the present invention provide water-proof products which may be applied to the lips, skin, or eyelashes more easily. In addition, the non-aqueous cosmetic compositions of the present invention dry better to provide wetter looking products than prior art non-aqueous cosmetics. The amount of dispersing agent found sufficient to enable the increase in solids content in the non-aqueous cosmetic composition of the present invention is in the range of about 0.05 weight percent to about 3.5 weight percent, preferably about 0.1 weight percent to about 0.5 weight percent of the total cosmetic compostion.

The dispersing agents found useful in the cosmetic compositions of the present invention are polymeric acid amines formed by condensing a polymeric acid with an amine and removing the so-formed water. See, for example, U.S. Pat. No. 4,349,389 at Col. 5, lines 5–35. The polymeric acid is a polyester derived from a hydrocarbon acid of the formula:

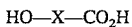

HO—X—CO$_2$H wherein X is a divalent saturated or unsaturated aliphatic carbon chain which may be interupted by O, N or S and preferably contains from 8 to 250 carbon atoms, more preferably 12 to 50 carbons and in which there are at least 4 atoms, preferably 4 carbon atoms between the hydroxy and the carboxylic groups or from a mixture of such a hydroxy carboxylic acid and a carboxylic acid which is free from hydroxy groups. Preferred hydroxy acids of the formula HO—X—CO$_2$H are hydroxy substituted (C$_{12}$–C$_{20}$) alkanoic acid. Hydroxy fatty acids such hydroxystearic acid disclosed in U.S. Pat. No. 4,349,389 are preferred.

The amines used to form the polymeric acid amine are lower alkylamine, di-or tri-lower alkylamines and di- and polyamines such as diloweralkylaminoloweralkylamine. The term "loweralkyl" means straight or branched chain alkyl groups of one to six carbons such as methyl, ethyl, n, and iso propyl, n, sec, iso and terbutyl and the like. Typically suitable amines include methylamine, diethylamine, triethylamine, dimethylaminopropylamine, ethylenediame, triethylenetetramine, quanidine and derivatives thereof. The preferred dispersing agents include Solsperse, especially Solsperse 9000 but also Solsperse 3000 available from ICI Americas Inc., Wilmington, Del. 19897 and those disclosed in U.S. Pat. Nos. 4,349,389, 3,778,287 and 4,157,266 especially in the examples of each patent.

The terms "dry powders" as used herein means talc, fillers (e.g. nylon and silica) as well as nacreous or pearlescent materials such as natural pearl, titanium dioxide, bismuth oxychloride, bismuth oxychloride on mica, titanium dioxide coated mica (titanated mica) and crystals of quanine.

Typical suitable cosmetic waxes include ozokerite, lanolin alcohol, paraffin wax, bayberry wax, Polawax (a reaction product of higher fatty alcohols and ethylene oxide available from Croda, Inc., New York, N.Y. 10016), trihydroxystearin, lanolin wax, beeswax, candelilla wax, microcrystalline wax, carnauba wax, cetyl alcohol, stearyl alcohol, synthetic spermaceti, cocoa butter, fatty acids of lanolin, mono-, di- and triglycerides which are solid at 25 C, e.g., glyceryl tribehenate, a triester of behenic acid and glycerine and $C_{18}$–$C_{36}$ acid triglyceride, a mixture of triesters of $C_{18}$–$C_{36}$ carboxylic acids and glycerine available from Croda, Inc., New York, N.Y. under the tradenames Syncrowax HRC and Syncrowax HGL-C, respectively, fatty esters which are solid at 25 C, silicone waxes such as methyloctadecaneoxypolysiloxane and poly (dimethylsiloxy) stearoxysiloxane, stearyl mono- and diethanolamide, rosin and its derivatives such as the abietates of glycol and glycerol, hydrogenated oils solid at 25 C, and sucroglycerides.

Typical suitable cosmetic oils include mineral oil, Purcellin oil, perhydrosqualene, castor oil, polybutene, odorless mineral spirits, sweet almond oil, avocado oil, calophyllum oil, ricin oil, vitamin E acetate, olive oil, silicone oils such as dimethicone, dimethylpolysiloxane and cyclomethicone, linolenic alcohol, oleyl alcohol, the oil of cereal germs such as the oil of wheat germ, isopropyl palmitate, isopropyl myristate, butyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Typical suitable cosmetic solids or semi-solids include lanolin, hydrogenated lanolin, hydroxylated lanolin, acetylated lanolin, petrolatum, isopropyl lanolate, cetyl myristate, myristyl myristate, myristyl lactate, cetyl alcohol, isostearyl alcohol and isocetyl lanolate.

It is preferred to employ a mixture of these cosmetic ingredients for their different functions, for example oleyl alcohol is a pennant and color vehicle, castor oil is a color dispersing agent in for example lipstick and eyeliners, mineral oil and cyclomethicone are emollients and moisturizers.

The cosmetic compositions of the present invention may also include other ingredients, for example, sunscreens, antioxidants, preservatives, moisturizers, surfactants, bodying agents and suspending agents.

Typical suitable sunscreens include titanium dioxide, zinc oxide, certain esters of salicylic acid, e.g. homomenthyl salicylate, alkyl esters of paramethoxycinnamate, e.g. octyl methoxycinnamate and certain benzophenone derivatives, e.g. benzophenone-3 and substituted para-aminobenzoates e.g. octyl dimethyl PABA.

Typical suitable antioxidants include propyl, octyl and dodecyl esters of gallic acid, butylated hydroxyanisole, i.e., BHA which is a mixture of 3-tert-butyl-4-hydroxyanisole (major) and 2-tert-butyl-4hydroxyanisole, butylated hydroxytoluene and nordihydroguaiaretic acid.

Typical suitable preservatives include the lower alkyl esters of para-hydroxybenzoates (paraben) especially, methyl paraben, ethyl paraben, n-propyl paraben, n-butyl paraben, isobutyl paraben and mixtures thereof, imidazolidinyl urea, or diazolidinyl urea.

Typical suitable moisturizers include butylene glycol, propylene glycol, reticulin (the protein) available from Croda, Inc., New York, N.Y. 10016, saccharide isomerate available from Centerchem, Inc. New York, N.Y., and vitamin E acetate.

Typical suitable surfactants include nonionic, anionic and cationic surfactants such as sorbitan stearate, and oleth-3 phosphate respectively.

Polymers may be used to achieve either one or a combination of effects. Polymers may, for example, serve as suspending aids, emulsion stabilizers, emulsification aids, binders, thickeners or film formers, or may provide water resistancy, water proofing or gloss. Typical suitable polymers include polyethylene, methylcellulose, hydroxyethylcellulose; vinyl polymers and copolymers, e.g., polyvinyl pyrrolidone (PVP) homopolymers and PVP copolymers such as PVP/eicosene copolymer, PVP/hexadecene copolymer; polyvinylacetate (PVA) homopolymers and PVA copolymers; ethylene oxide homopolymers/copolymers and derivatives; and acrylic polymers, e.g., acrylic/acrylate copolymers.

Typical suitable bodying agents include Carbomers, especially Carbomer 934 P, which are polymers of acrylic acid cross-linked with a polyfunctional agent and available from B. F. Goodrich Chemical Co. under the Carbopol tradename; methylcellulose, hydroxyethylcellulose and polyacrylates.

Typical suitable suspending agents, useful for suspending pigments, include magnesium aluminum silicate, polybutene and Bentone Gels, the tradename of N.L. Chemicals, Div. of NL Industries for a series of modified (by cation exchange reaction with an organic base, such as quaternary ammonium salt) hectorites (one of montmorillonite minerals that are the principal constituents of bentonite clay).

The compositions of the present invention used in the form of lipstick are formulated from cosmetically acceptable liquids, and colorants and stiffened to the desired consistency with cosmetically acceptable waxes which also raise the melting point and improve the physical stability.

The compositions of the present invention include colorants in the form of one or more organic pigments and inorganic pigments, which are usually dispersed in an oily vehicle.

Typical suitable organic pigments employed in the cosmetic compositions of the present invention are the Food, Drug and Cosmetic grade, e.g., D & C reds, oranges, yellows and blues. Typical suitable inorganic pigments include iron oxides, titanium dioxides, ultramarines, iron sulfides, or other conventional inorganic pigments approved for cosmetic use.

The amount of colorants employed in the lipstick cosmetic compositions of the present invention is in the range of from about 1% to about 10% by weight of the formulation with about 2% to about 4% being more preferred. The amount of colorants employed in the mascara and eyeliner cosmetic compositions of the present invention is in the range of from about 5% to about 30% by weight, preferably from about 7% to about 15% by weight of the composition.

Typically suitable solvents include odorless petroleum distillates, e.g., Shell Sol 71 available from Shell Chemical Co., odorless oil of turpentine, white spirits, volatile silicon oils, e.g., cyclomethicone (cyclic dimethyl polysiloxane), deca- or octamethylcyclopentasiloxane, ethanol and/or isopropyl alcohol (which also functions as a viscosity control agent) and the like.

A typical eyeliner or mascara may contain one or more volatile components, e.g. isopropyl alcohol, one or more inorganic polymers for thickness, e.g., montmorillonite clay, one or more waxes as viscosity aids, as well as antioxidants, preservatives and processing aids, e.g., dimethicone which is a mixture of fully methylated siloxane polymers end-blocked with trimethylsiloxy units.

The lipstick compositions of the present invention may also include thickening and suspending agents for the organic and inorganic pigments. Typical suitable thickening and suspending agents include stearalkonium Hectorite, a reaction product of Hectorite (one of the montmorillonite minerals that are the principal constituents of bentonite clay) and stearalkonium chloride [a quarternary ammonium salt of the formula, $[CH_3(CH_2)_{16}CH_2—N—(CH_3)_2—CH_2—C_6H_5]$ Cl].

GENERAL EXPERIMENTAL

The suppliers of other ingredients used in the following illustrative examples can be found in CTFA Cosmetic Ingredient Dictionary, Third Edition, 1982, N. F. Estrin et al., eds., published by The Cosmetic, Toiletry and Frangrance Association, Inc., 1110 Vermont Avenue, N.W., Wash. D.C. 20005. For convenience, the following examples illustrate only Solsperse 9000 (Hypermer LP 4) as the dispersing agent, but other dispersing agents as described hereinabove could similarly be used to permit an increased solid content the non-aqueous cosmetics of this invention.

EXAMPLES 1–2

| | Mascara Comparative Examples | |
|---|---|---|
| | Example No. | |
| Ingredients | 1 weight % | 2 weight % |
| Part A | | |
| Isopar E[1] | 15.00 | 15.00 |
| Pentaerythritol Tetraabietate | 7.00 | 7.00 |
| Part B | | |
| Isopar E | 37.32 | 39.57 |
| Aluminum Stearate | 2.00 | 2.00 |
| Polybutene | 1.00 | 0.50 |
| Magnesium Aluminum Silicate | 1.00 | 1.00 |
| Part C | | |
| Bayberry Wax | 2.50 | 2.50 |
| Polyethylene | 15.00 | 15.00 |
| Beeswax | 4.00 | 4.00 |
| Lanolin, Anhydrous | 1.50 | 1.00 |
| Candelilla Wax | 3.00 | 3.00 |
| Methylparaben | 0.20 | 0.20 |
| Propylparaben | 0.10 | 0.10 |
| Butylparaben | 0.10 | 0.10 |
| BHA | 0.03 | 0.03 |
| Part D | | |
| Black 3190 | 10.00 | 9.00 |
| Part E | | |
| Solsperse 9000[2] | 0.25 | — |

[1] $C_8$–$C_9$ isoparaffin available from EXXON Co., U.S.A., Houston, Texas.
[2] Also known as Hypermer LP4

In a steam jacketed mixing kettle equipped with a stirrer, heat a mixture of the ingredients in Part A to 70°–85° C. with mixing until a homogenous solution is formed. To a separate container, add with mixing the ingredients in Part B and heat the mixture so formed to 50°–65° C. Add Part B to Part A and heat with mixing to 70°–75° C. In a separate container, add the ingredients in Part C and heat to 95°–100° C. until the waxes are melted. Add the melted waxes of Part C to the mixture of A & B. To the so formed mixture, add the Solsperse of Part E. To the so formed mixture, add the pigment of Part D. Cool the so formed to 70°–75° C. and pass the so formed mixture through a colloid mill until the pigment is dispersed. Force cool to 40 to 45 and fill into containers.

EXAMPLES 3–5

| | Eyeliner | | |
|---|---|---|---|
| | Example No. | | |
| Ingredient | 3 weight % | 4 weight % | 5 weight % |
| Part A | | | |
| Beeswax | 7.00 | 7.0 | 7.0 |
| Ganex V-216[1] | 7.5 | 7.5 | 7.5 |
| BHA | 0.03 | 0.03 | 0.03 |
| Butylparaben | 0.30 | 0.30 | 0.30 |
| Propylparaben | 0.15 | 0.15 | 0.15 |
| Simethicone | 0.10 | 0.10 | 0.10 |
| Part B | | | |
| Shell-Sol 71[2] | 3.92 | — | 4.67 |
| Bentone Gel SS71 | 60.00 | 56.92 | 60.00 |
| Part C | | | |
| Solsperse 9000 | 1.00 | 3.00 | 0.25 |
| Part D | | | |
| Black Oxide | 20.00 | 25.00 | 20.00 |

[1] Copolymer of hexadecene and vinyl pyrrolidone available from GAF Corp., Wayne, NJ.
[2] A complex mixture of predominably branched chain saturated $C_9$–$C_{12}$ hydrocarbons available from Shell Chemical Co., Houston, Texas.

In a steam jacketed mixing kettle equipped with a stirrer, mix the ingredients in Part B and heat the mixture to 75° C. In a separate kettle heat the ingredients in Part A to 70°–75° C. and add to Part B. Add Solsperse of Part C to the mixture of Parts A & B and mix until a homogenous mixture is formed. To the so formed mixture add the pigment of Part D and pass the so formed mixture through a colloid mill until the pigment is dispersed. Force cool the so formed dispersion to 40°–45° C. and fill into containers.

EXAMPLES 6–8

| | Pen Eyeliner | | |
|---|---|---|---|
| | Example No. | | |
| Ingredients | 6 weight % | 7 weight % | 8 weight % |
| Part A | | | |
| Shel Sol 71 | 17.57 | 17.57 | 21.57 |
| Bentone Gel SS-71 | 20.00 | 20.00 | 20.00 |
| Glyceryl Hydrogenated Rosinate | 5.00 | 5.00 | 7.00 |
| Isopar E | 25.00 | 25.00 | 25.00 |

-continued

| | Pen Eyeliner | | |
|---|---|---|---|
| | Example No. | | |
| Ingredients | 6 weight % | 7 weight % | 8 weight % |
| Part B | | | |
| Solsperse 9000 | 2.00 | 2.00 | 1.00 |
| Part C | | | |
| Mango Violet | 30.00 | — | 20.00 |
| Brown Color Mix | — | 30.00 | — |
| TiO$_2$ | — | — | 5.00 |
| Part D | | | |
| Methylparaben | 0.10 | 0.10 | 0.10 |
| Propylparaben | 0.10 | 0.10 | 0.10 |
| Butylparaben | 0.10 | 0.10 | 0.10 |
| BHA | 0.03 | 0.03 | 0.03 |
| Part E | | | |
| Phenoxyethanol | 0.10 | 0.10 | 0.10 |

In a steam jacketed mixing kettle equipped with a stirrer, add the Shell Sol and Isopar of Part A to the Bentone Gel and mix until a homogeneous mixture is formed. Heat the mixture to 80°–85° C. and add the glyceryl hydrogenated rosinate with mixing until a homogeneous mixture is formed. Add thereto the Solsperse of Part B with mixing. Add the pigments of Part C with continued mixing. Add the ingredients of Part D. Pass the so formed mixture through a colloid mix at 70°–75° C. until the pigments are dispersed. Force cool the dispenser to 35° C.; add the phenoxyethanol and force cool to room temperature.

EXAMPLE 9

| | Mascara |
|---|---|
| Ingredient | weight % |
| Part A | |
| Pentaorythritol Tetraabietate | 8.00 |
| Shell Sol 71 | 15.00 |
| Part B | |
| Shell Sol 71 | 19.00 |
| Aluminum Stearate | 2.25 |
| Bentone Gel SS71 | 5.00 |
| Part C | |
| Shell Sol 71 | 7.97 |
| Part D | |
| Carnauba Wax | 1.00 |
| Polyethylene | 17.00 |
| Lanolin, Anhydrous USP | 1.25 |
| Butylparaben | 0.10 |
| Propylparaben | 0.10 |
| Methylparaben | 0.20 |
| BHA | 0.03 |
| Part E | |
| Solsperse 9000 | 0.1000 |
| Blue, Ultramarine | 8.00 |
| Part F | |
| Shell Sol 71 | 11.00 |
| Part G | |
| Shell Sol 71 | 4.00 |

Into a steam jacketed kettle equipped with a stirrer, add the Shell Sol of Part A. With slow mixing, raise the temperature to 105°–110° C. and add the pentaerylthritol tetraabietate. Continue stirring until a translucent solution results. Turn off the steam. Into a second steam jacketed tank equipped with double stirrers, add the Shell Sol of Part B and gradually add the aluminum stearate. Stir and continue stirring until a homogeneuos dispersion is formed. Raise the temperature of Part B to 50°–55° C. and add the Bentone Gel of Part B. The so formed mixture is stirred until a homogeneous dispersion is formed. Add thereto the solution of Part A. Rinse kettle used to prepare solution of Part A with the Shell Sol of Part C and add the rinse to kettle containing Parts A & B. Raise temperature of the mixture of Parts A & B to 88°–92 C. and increase the stirring speed. Slowly add the polyethylene of Part D in portions and thereafter the other ingredients in Part D while maintaining the temperature at 88°–92° C. Stir until a translucent solution results. Add the Solsperse of Part E and stir. Add the Blue pigment of Part E and continue mixing. Add the Shell Sol of Part F and cool to 68°–72° C. with continued mixing. Maintaining the temperature of the so formed mixture at 68°–72° C. and pass it through a colloid mill. Rinse colloid mill with Shell Sol of Part G and add the rinse to the mixture. Force cool the mixture to 50°–55° C. Fill the so formed mixture into mascara applicators.

EXAMPLES 10

| I. Preparation of Mango Violet Extender Formula | |
|---|---|
| Ingredients | % w/w |
| Cosmetic Manganese Violet | 45.000 |
| Solsperse 9000 | 1.000 |
| Castor Oil | 53.800 |
| Tenox 2 | 0.050 |
| Propylparaben | 0.150 |

Into a kettle equipped with an agitator, add and mix the above listed ingredients at 25° C. until the cosmetic manganese violet is homogeneously dispersed in the castor oil. Twice pass the so-formed homogeneous dispersion through a triple roller mill. Add the twice-milled dispersion into a kettle equipped with an agitator and mix until a homogeneous dispersion is formed. This dispersion is hereinafter called "Magno Violet Extender Formula".

In prior art extender formulas prepared without Solsperse 9000, only 30% by weight cosmetic manganese violet could be added. Attempts to increase the manganese violet content above 30% by weight produced unacceptable, nonhomogeneous dispersions.

| II. Preparation of a Lipstick Formula with Solsperse 9000 (Hypermer LP 4) | |
|---|---|
| | % w/w |
| Part A | |
| Magno Violet Extender Formula | 9.913 |
| Titanium Dioxide | 1.000 |
| Part B | |
| Candelilla Wax | 5.286 |
| White Ozokerite | 6.728 |

-continued

| II. Preparation of a Lipstick Formula with Solsperse 9000 (Hypermer LP 4) | |
|---|---|
| | % w/w |
| Lanolin Wax | 3.338 |
| Carnauba Wax | 0.961 |
| Cetyl Alcohol | 1.443 |
| Hydrogenated Vegetable Oil | 5.284 |
| Bentone Gel CAO | 12.013 |
| Arachidyl Propionate | 5.286 |
| Lanolin Oil | 7.790 |
| Acetylated Lanolin Alcohol | 11.054 |
| Trihydroxystearin | 0.950 |
| Polybutene | 3.870 |
| Oleyl Alcohol | 5.766 |
| Acetylated Lanolin | 6.824 |
| BHA | 0.048 |
| Propylparaben | 0.190 |
| Butylparaben | 0.095 |
| Methylparaben | 0.095 |
| Part C | |
| Colorona Magenta | 3.689 |
| Mica + Titanium dioxide + Carmine | 6.100 |
| Bismuth Oxychloride + Castor Oil | 1.300 |
| Part D | |
| Castor Oil | q.s. 100.000 |

Into a kettle equipped with an agitator, add 9.913 parts of the Magno Violet Extender and 1.000 parts of titanium dioxide and mix until uniform. This is Part A. Into a stainless steel steam-jacketed kettle equipped with a double motion agitator, add all the waxes in Part B and heat at 80°–85° C. until all the waxes are melted. Add thereto all the remaining ingredients in Part B and mix at 80°–85° C. until a homogeneous mixture is formed. Continue mixing while slowly cooling the mixture to 70°–75° C. and filter the mixture through cheese cloth. Add the filtered mixture to a stainless steel steam-jacketed kettle equipped with an agitator and mix at 80°–83° C. until a homogeneous mixture is formed. Add thereto the ingredients in Part C and continue mixing until a homogeneous dispension is formed. Add thereto Part A and mix at 80° C. until uniform. Add thereto Part D at 80° C. and mix until uniform. Cool to 70°–75° C. and continue mixing for about 1 hour. Filter the so formed mixture through cheese cloth and store in appropriate containers.

What is claimed is:

1. A non-aqueous eyeliner composition comprising about 7% by weight beeswax, about 7.5% by weight of a copolymer of hexadecene and vinyl pyrrolidone, from about 0% to about 5% by weight of solvent comprising a mixture of branched chain saturated $C_9$–$C_{12}$ hydrocarbons, from about 57% to about 60% by weight of organophilic clay gel suspending agent comprising hectorite clay modified by cation exchange reaction with quaternary ammonium salt, from about 0.25% to about 3.0% by weight of a dispersing agent comprising a polymeric acid amine which is a condensation product of an hydroxy acid of the formula HO—X—COOH, or (b) a mixture of the hydroxy acid of the formula and a carboxylic acid which is free from hydroxy groups, with an amine selected from the group consisting of lower alkyl amines, di-lower alkyl amines, tri-lower alkyl amines, and di-lower alkyl amino lower alkyl amines, wherein lower alkyl means straight or branched alkyl groups of 1 to 6 carbon atoms, and X is a divalent saturated or unsaturated aliphatic carbon chain which may be interrupted by O, N or S and contains 12 to 50 carbon atoms, with at least four carbon atoms separating the hydroxy and carboxylic groups, and from about 20 to about 25% by weight of cosmetically acceptable colorant.

2. The eyeliner composition of claim 1 wherein the hydroxy acid of the formula is a mono hydroxy substituted $C_{12}$–$C_{20}$ alkanoic acid.

3. The eyeliner composition of claim 1 wherein the hydroxy acid of the formula is hydroxystearic acid.

* * * * *